US005399169A

United States Patent [19]
Stein

[11] Patent Number: 5,399,169
[45] Date of Patent: Mar. 21, 1995

[54] ONE-HAND NEEDLE CAPPING SYSTEM

[76] Inventor: Daniel T. Stein, 2415 Buckeye St., Newport Beach, Calif. 92660

[21] Appl. No.: 255,074

[22] Filed: Jun. 7, 1994

Related U.S. Application Data

[63] Continuation of Ser. No. 52,109, Apr. 23, 1993, abandoned.

[51] Int. Cl.6 ........................ A61M 5/32; B65D 83/10
[52] U.S. Cl. ...................................... 604/192; 206/365
[58] Field of Search ...................... 604/192, 263, 110; 128/919; 206/364–366, 370

[56] References Cited

U.S. PATENT DOCUMENTS

| 4,248,246 | 2/1981 | Ikeda | 128/765 |
| 4,380,292 | 4/1983 | Cramer | 206/366 |
| 4,717,386 | 1/1988 | Simmons | 604/192 |
| 4,737,149 | 4/1988 | Gillilan . | |
| 4,777,964 | 10/1988 | Briggs et al. | 128/760 |
| 4,826,488 | 5/1989 | Nelson . | |
| 4,830,319 | 5/1989 | Willoughby | 248/176 |
| 4,852,844 | 8/1989 | Villaveces . | |
| 4,890,734 | 1/1990 | Gach | 206/366 |
| 4,915,225 | 4/1990 | Tabor | 206/368 |
| 4,915,698 | 4/1990 | Levenson . | |
| 4,919,264 | 4/1990 | Shinall | 206/210 |
| 4,921,199 | 5/1990 | Villaveces | 248/314 |
| 4,936,449 | 6/1990 | Conard et al. | 206/366 |
| 4,979,945 | 12/1990 | Wade . | |
| 5,012,622 | 5/1991 | Sato et al. | 52/725 |
| 5,024,326 | 6/1991 | Sandel et al. | 206/366 |
| 5,178,157 | 1/1993 | Fanlo | 128/763 |
| 5,209,738 | 5/1993 | Bruno | 604/192 |
| 5,311,985 | 5/1994 | Suida | 206/210 |

FOREIGN PATENT DOCUMENTS 2198644  6/1988  United Kingdom ................ 604/192

Primary Examiner—John D. Yasko
Assistant Examiner—Alan J. Cermak

[57] ABSTRACT

A "one-hand" needle capping system utilizing a bed of nontoxic, nonhardening clay for reapplying a protective cap to a needle of a syringe.

10 Claims, 1 Drawing Sheet

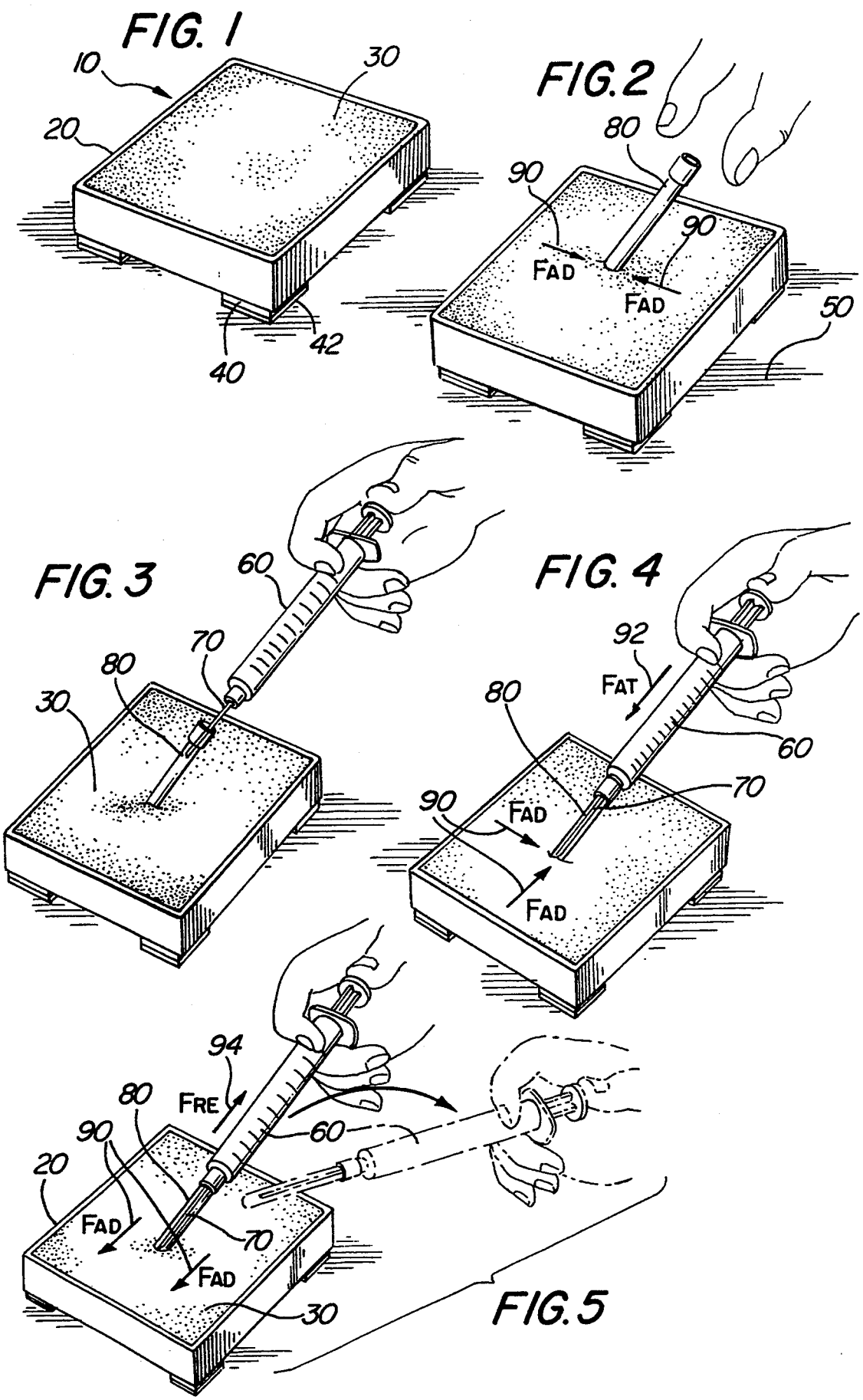

ONE-HAND NEEDLE CAPPING SYSTEM

This is a continuation of application Ser. No. 08/052,109, filed on Apr. 23, 1993, for a ONE-HAND NEEDLE CAPPING SYSTEM (now abandoned).

BACKGROUND OF THE INVENTION

1. Field of the Invention

The present invention relates to needle capping systems and, more particularly, pertains to a one-hand needle capping system.

2. Description of Related Art

The art is generally cognizant of needle capping systems which utilize a variety of mechanisms for protecting medical personnel from accidental needlesticks and for removing caps from syringe needles. Representative prior art in the field of needle capping systems is included below.

T. A. Gillilan, U.S. Pat. No. 4,737,149, discloses a resilient shield assembly for use in engaging a protective sheath releasably mounted on a syringe needle assembly.

R. A. Nelson et al., U.S. Pat. No. 4,826,488, teaches a hypodermic syringe needle guard in the form of a cylindrical cap which slides over the needle, having a manipulating device to remove and replace the needle guard.

J. W. Villaveces, U.S. Pat. No. 4,852,844, discloses a frustro-conical hollow member supported by a backing plate.

M. F. Levenson, U.S. Pat. No. 4,915,698, teaches another tubular member extending from a base member at a predetermined angle constituting a device for removing and replacing needle covers on syringes.

S. E. Wade et al., U.S. Pat. No. 4,979,945, discloses a syringe needle protector and remover designed for three different standard needle cap shapes.

These needle recapping systems fail to optimally meet the needs of medical personnel. Today's medical care often entails the use of syringes or other piercing devices for introducing medication into the body of a patient or for withdrawing fluids for analysis. Accordingly, the medical practitioner or those in the practitioner's assisting staff are often exposed to the risk of inadvertent injury, a risk of substantial consequence in the case of treatment of contagious diseases. Hypodermic needles of the type used for injections or for drawing blood samples generally include a removable protective cover or cap which protects the needle and helps to keep it sterile in storage until used. It has become a conventional medical procedure to replace the cap on a used, "contaminated" needle ("recap") to prevent accidental needlesticks. Unfortunately, no device for eliminating the risk of needlesticks during recapping which is simple, free of complex mechanisms, able to hold protective caps of different sizes, and able to hold protective caps at varying angles, is known. Furthermore, the art is devoid of a needle recapping system embodying the above features which is also safe, easy to assemble, renewable, inexpensive, virtually without mechanical parts subject to wear, and does not require modification of the hypodermic needle and cap itself.

OBJECTS AND SUMMARY OF THE INVENTION

An object is to provide a needle recapping system which holds a protective cap so that medical personnel need not risk needlesticks during the recapping process, a "one-hand" needle capping system meeting OSHA regulations.

Another object is to provide a needle capping system which accommodates protective caps of different sizes and which holds them at a variety of different angles.

Still another object is to provide a needle capping system which is safe, easy to assemble, inexpensive, renewable, virtually without mechanical parts subject to wear, and does not require modification of the standard hypodermic syringe and needle cap.

The one-hand needle capping system includes a tray within which is contained a bed of nontoxic, nonhardening clay. The tray is supported by several feet for detachably mounting the tray to a surface near a patient who is to receive an injection. When the protective cap of a syringe is removed, the medical professional thrusts the protective cap into the bed of clay. The clay is sufficiently pliant and sufficiently adhesive to engulf and adhere to the protective cap and to hold the protective cap in a substantially stationary position while the syringe is being used. The clay bed is characterized as having an adhesive force sufficiently strong to hold the protective cap when the protective cap is being resecured to the syringe. Furthermore, the adhesive force is not so strong that it will not release the protective cap when the syringe is pulled from the clay bed, after the syringe has been resecured to the protective cap.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein:

FIG. 1 is a schematic perspective showing a one-hand needle capping system;

FIG. 2 is a schematic perspective of a one-hand needle capping system into which a protective cap has been placed;

FIG. 3 is a schematic perspective of a one-hand needle capping system into which a protective cap has been inserted and wherein a medical professional is resecuring a syringe with an attached needle to the protective cap which is being supported by a clay bed;

FIG. 4 is a schematic perspective of a one-hand needle capping system which is supporting a protective cap while a syringe and attached needle are resecured to the protective cap; and FIG. 5 is a schematic perspective of a one-hand needle capping system showing how a medical professional removes the syringe, needle, and resecured protective cap from the clay bed.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a one-hand needle capping system utilizing a nontoxic, nonhardening clay.

FIG. 1 shows a one-hand needle capping system 10 which includes a tray 20, a bed of nontoxic, nonhardening clay 30, and a plurality of support feet 40. Tray 20 is a receptacle or container within which the clay bed 30 is placed. In a preferred embodiment, tray 20 is made of a polystyrene plastic and appears rectangular or square in shape. During the assembly of the one-hand needle capping system 10, the nontoxic, non-hardening clay bed 30 is pressed into tray 20. Clay bed 30, which, in a preferred embodiment, is a modeling clay, conforms to the shape of tray 20.

Needle capping system 10 additionally includes a plurality of support feet 40 which are detachably mounted to tray 20. As illustrated in FIG. 1, support feet 40 are preferably attached to the underside of tray 20. Additionally, an adhesive layer 42 is included on the underside of each support foot 40. Adhesive layer 42 may be an adhesive tape or other means for detachably mounting each of the support feet to a surface to which the needle capping system 10 is to be attached, thereby detachably mounting tray 20 and the clay bed 30 contained therein to such a surface.

Needle capping system 10, as illustrated in FIGS. 1–5, provides a "one-hand" needle capping system meeting OSHA regulations. More specifically, needle capping system 10 obviates the need for using two hands to recap a syringe. This eliminates medical personnel being subjected to needlesticks during recapping. Furthermore, needle capping system 10 embodies a method of reapplying a protective cap to a needle of a syringe complying with the aforementioned OSHA regulations. As seen in FIG. 2, needle capping system 10 is secured by adhesive layer 42 on the underside of each support foot 40 to a surface 50 near a patient who is to receive an injection. FIG. 3 shows that syringe 60 includes attached needle 70 and protective cap 80, which fits over needle 70.

After removal of protective cap 80 from syringe 60, a medical professional simply thrusts protective cap 80 into the clay bed 30 contained within tray 20. Clay bed 30 is sufficiently pliant and sufficiently adhesive to engulf and adhere to protective cap 80 when protective cap 80 is thrust into clay bed 30. FIG. 2 shows an adhesive force ($F_{AD}$) 90 acting upon protective cap 80 after it is thrust into clay bed 30. Adhesive force 90 is sufficiently strong to hold protective cap 80 in a substantially stationary position while syringe 60 is used to administer an injection. Needle capping system 10 is particularly advantageous in that it accommodates protective caps 80 of different sizes and is capable of holding such protective caps 80 at a variety of different angles.

FIG. 3 illustrates the reinsertion of syringe 60 and attached needle 70 into protective cap 80 supported by clay bed 30. The reinsertion of needle 70 into protective cap 80 necessarily involves application of an attaching force ($F_{AT}$) 92 to syringe 60, as shown in FIG. 4. Attaching force 92 is not necessarily limited to a linearly directed force which snaps protective cap 80 back onto syringe 60 and over needle 70; it may also be a twisting force if syringe 60 and protective cap 80 are designed to reattach in such a manner. The adhesive force 90 of clay bed 30 is sufficiently strong to secure protective cap 80 within clay bed 30 while protective cap 80 is resecured to syringe 60 by attaching force 92, which is applied to syringe 60 by a medical professional, as seen in FIG. 4.

After protective cap 80 is reattached to syringe 60, protective cap 80 is pulled from clay bed 30, as seen in FIG. 5. The pulling of syringe 60 results in the application of a removing force ($F_{RE}$) 94 to syringe 60. Adhesive force 90 resists releasing protective cap 80 from clay bed 30; however, adhesive force 90 is overcome by force 94 and releases protective cap 80 from clay bed 30.

After protective cap 80 is removed from clay bed 30, an indentation may be left in clay bed 30 where protective cap 80 had been inserted. Such an indentation is easily removed from clay bed 30 by reshaping by hand the clay bed 30 within tray 20.

Accordingly, needle capping system 10 provides a "one-hand" needle capping system which is safe, easy to assemble, inexpensive, renewable, and virtually without mechanical parts subject to wear.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An apparatus for holding a protective cap from a needle of a syringe while the needle and syringe are used and while the needle is reinserted into the protective cap, and for releasing the cap when the recapped needle and syringe are removed, the apparatus comprising:
    a tray;
    a bed of nontoxic, nonhardening clay contained within the tray for engulfing and adhering to a protective needle cap when the protective cap is thrust into the clay bed, for holding the protective cap in a substantially stationary position while the needle and syringe are used and while the needle is reinserted into the cap and for releasing the protective cap from the clay bed when the cap, attached to the needle and syringe, is removed from the clay bed; and
    means for detachably mounting the tray so that the tray remains stationary when the cap is thrust into the clay bed and when the cap, attached to the needle and syringe, is removed from the clay bed.

2. The apparatus of claim 1, wherein the tray is made from a polystyrene plastic.

3. The apparatus of claim 1, wherein nontoxic, nonhardening clay is a modeling clay.

4. The apparatus of claim 1, wherein the means for mounting comprises:
    a plurality of feet attached to the tray for supporting the tray when detachably mounted to a substantially stationary surface.

5. The apparatus of claim 4, wherein each of the feet further includes an adhesion means for adhering each foot to ensure that the tray remains stationary.

6. A device for temporarily holding a protective cap from a needle so that the needle can be recapped using only one hand, the device comprising:
    a tray including a substantially planar base with sides disposed about a periphery of the base;
    mounting means on an under surface of the base for ensuring that the tray remains stationary; and
    a bed of nontoxic, pliable material disposed within the tray for holding a protective needle cap at an angle selected by a user inserting the cap into the bed so that a needle can be conveniently recapped using only one hand by reinserting the needle into the held cap.

7. The device of claim 6, wherein the mounting means comprises:
   a plurality of feet attached to the tray for supporting the tray when detachably mounted to a substantially stationary surface.

8. The apparatus of claim 7, wherein each of the feet further includes an adhesion means for adhering each foot to ensure that the tray remains stationary.

9. A method of recapping a needle using one hand, the method comprising the steps of:
   providing a tray containing a bed of a nontoxic pliable substance, the tray detachably mounted so that it remains stationary;
   removing a protective cap from a needle;
   inserting the cap into the bed of pliable substance at a convenient angle so that the cap is held by the substance at the convenient angle;
   holding the needle with one hand; and
   inserting the needle into the cap held at the convenient angle by the pliable substance so that the needle is safely recapped and the recapped needle may then be removed from the pliable substance.

10. A device for temporarily holding a protective cap from a needle so that the needle can be recapped using only one hand, the device comprising:
   a tray including a substantially planar base with sides disposed about a periphery of the base;
   mounting means on an under surface of the base for ensuring that the tray remains stationary; and
   a bed of nontoxic, pliable modeling clay disposed within the tray for providing an adhesion force to hold a protective needle cap at an angle selected by a user inserting the cap into the bed and to resist an attaching force applied to the cap when reinserting the needle into the cap so that a needle can be conveniently recapped using only one hand by reinserting the needle into the held cap.

* * * * *